(12) United States Patent
Corma Canos et al.

(10) Patent No.: US 10,207,973 B2
(45) Date of Patent: Feb. 19, 2019

(54) METHOD FOR PRODUCING 1-OCTANOL

(71) Applicant: Abengoa Bioenergia Nuevas Tecnologias, S.A., Seville (ES)

(72) Inventors: Avelino Corma Canos, Seville (ES); Marcelo Eduardo Domine, Seville (ES); Juan Luis Sanz Yague, Seville (ES); Francisco Antonio Ladron de Guevara Vidal, Seville (ES)

(73) Assignee: Abengoa Bioenergia Nuevas Tecnologias, S.A., Seville (ES)

( * ) Notice: Subject to any disclaimer, the term of this patent is extended or adjusted under 35 U.S.C. 154(b) by 0 days.

(21) Appl. No.: 15/525,963

(22) PCT Filed: Nov. 12, 2015

(86) PCT No.: PCT/ES2015/070812
§ 371 (c)(1),
(2) Date: May 11, 2017

(87) PCT Pub. No.: WO2016/075353
PCT Pub. Date: May 19, 2016

(65) Prior Publication Data
US 2017/0320799 A1   Nov. 9, 2017

(30) Foreign Application Priority Data

Nov. 14, 2014   (ES) .................................. 201431672

(51) Int. Cl.
| | | |
|---|---|---|
| *C07C 29/34* | (2006.01) | |
| *B01J 23/00* | (2006.01) | |
| *B01J 23/62* | (2006.01) | |
| *C07C 29/32* | (2006.01) | |
| *B01J 37/08* | (2006.01) | |
| *B01J 23/08* | (2006.01) | |
| *B01J 23/44* | (2006.01) | |
| *B01J 23/648* | (2006.01) | |
| *B01J 23/72* | (2006.01) | |
| *B01J 23/89* | (2006.01) | |
| *B01J 21/10* | (2006.01) | |
| *B01J 37/02* | (2006.01) | |
| *B01J 37/03* | (2006.01) | |
| *B01J 37/06* | (2006.01) | |

(52) U.S. Cl.
CPC ............... *C07C 29/34* (2013.01); *B01J 21/10* (2013.01); *B01J 23/08* (2013.01); *B01J 23/44* (2013.01); *B01J 23/62* (2013.01); *B01J 23/6482* (2013.01); *B01J 23/72* (2013.01); *B01J 23/898* (2013.01); *B01J 37/0213* (2013.01); *B01J 37/0236* (2013.01); *B01J 37/036* (2013.01); *B01J 37/06* (2013.01); *B01J 37/08* (2013.01); *B01J 37/082* (2013.01); *C07C 29/32* (2013.01)

(58) Field of Classification Search
CPC ........... C07C 29/34; B01L 21/10; B01L 23/08
See application file for complete search history.

(56) References Cited

U.S. PATENT DOCUMENTS

2010/0160693 A1   6/2010   Kourtakis et al.

FOREIGN PATENT DOCUMENTS

| CN | 101530802 | 9/2009 |
|---|---|---|
| EP | 2 679 303 | 1/2014 |
| EP | 2 679 304 | 1/2014 |
| GB | 381185 | 9/1932 |
| GB | 849914 | 9/1960 |
| WO | WO 2009/026510 | 2/2009 |
| WO | WO 2009/097310 | 8/2009 |
| WO | WO 2009/097312 | 8/2009 |

OTHER PUBLICATIONS

Cosimo et al., *Structure and Surface and Catalytic Properties of Mg—Al Basic Oxides*, 178 Journal of Catalysis 499-510 (1998).
Nieto et al., *Preparation, characterization and catalytic properties of vanadium oxides supported on calcined Mg/Al-hydrotalcite*, 132 Applied Catalysis 41-59 (1995).
International Search Report and Written Opinion issued in corresponding International Patent Application No. PCT/ES2015/070812, dated Jan. 28, 2016.

*Primary Examiner* — Sikarl A Witherspoon
(74) *Attorney, Agent, or Firm* — Buchanan Ingersoll & Rooney PC

(57) ABSTRACT

The present invention relates to a process for obtaining 1-octanol which comprises a contact step between ethanol, n-hexanol and a catalyst, wherein said catalyst comprises: i) a metal oxide that comprises the following metals: M1 is at least one bivalent metal selected from Mg, Zn, Cu, Co, Mn, Fe, Ni and Ca; M2 is at least one trivalent metal selected from Al, La, Fe, Cr, Mn, Co, Ni, and Ga; ii) a noble metal selected from Pd, Pt, Ru, Rh and Re; and iii) optionally, comprises V; with the proviso that the catalyst comprises at least V, Ga or any of their combinations.

24 Claims, 4 Drawing Sheets

METHOD FOR PRODUCING 1-OCTANOL

The present invention relates to the preparation of 1-octanol by using a metal-oxide-type catalyst that comprises a noble metal and vanadium and/or gallium. Therefore, the present invention belongs to the field of catalytic processes for obtaining higher alcohols.

BACKGROUND ART

In recent years, numerous scientific publications and patents have appeared on the use of hydrotalcite-type materials as catalysts in alcohol condensation reactions, such as the Guerbet reaction, in both batch systems and fixed-bed continuous reactors. Most of the reactions described with such catalyst relate to the obtainment of n-butanol from ethanol. The studies performed with these mixed Mg—Al oxides revealed that the catalytic activity of these materials is dependent on the nature, density and strength of the basic surface sites, which, in turn, are dependent on the molar Mg/Al composition in the solid [J. I. Di Cosimo, V. K. Diez, M. Xu, E. Iglesia, C. R. Apesteguia, *J. Catal.* 178 (1998) 499;

In 1932, the BRITISH INDUSTRIAL SOLVENT Ltd. has claimed in GB381,185 that Mg—Al—Cu mixed oxides showed good activities for ethanol condensation to n-butanol. More recently, it has also established that hydrotalcite-derived mixed oxides based on Cu/Mg/Al show better catalytic activities in alcohols condensation than other analogous hydrotalcites, such as those including Ni supported species [C. Carlini, A. Macinai, M. Marchionna, M. Noviello, A. M. R. Galletti, G. Sbrana, *J. Mol. Catal. A: Chem.* 206 (2003) 409; X. Jiang, Z. Du, CN101530802 (2009)], among others.

In addition, international application WO2009026510 discloses a process for synthesising n-butanol by means of a material derived from the thermal decomposition of a hydrotalcite which preferably comprises magnesium and aluminium. Moreover, WO2009097312, US20100160693 and WO2009097310 disclose materials obtained by the thermal decomposition of hydrotalcites modified by the inclusion of metal carbonates and ethylenediamine-tetraacetates, which have been developed by DU PONT as catalysts in alcohol condensation reactions operating in a fixed bed at 300° C. and atmospheric pressure. The best results under these conditions have been achieved with a material derived from Cu—Mg—Al-based hydrotalcite (containing OH⁻ as the anion), which presents high ethanol conversion (≈44%) with moderate selectivities (≈44%) to n-butanol. When these same materials were assayed in the catalytic conversion of ethanol into n-butanol in the presence of hydrogen in the reaction system, the yields of n-butanol obtained were significantly lower in all cases.

Synthesis of high molecular weight alcohols (containing between 8-16 atoms of carbon) has become of interest in recent years due to the potential of these oxygenated compounds for use as surfactants and for addition to polymers, lubricants, cosmetics and many other specific uses. In particular, n-hexanol (n-HexOH), with an annual production of 450,000 kilograms, with a low value on the market focused on small scale supply to laboratories, could be transformed into more valuable 1-octanol (1-OctOH) or 1-decanol (n-DeOH).

1-OctOH and n-DeOH, with a world production exceeding 400,000 tonnes per year, are mainly used as surfactants and for addition to polymers, lubricants, cosmetics and many other specific uses.

Currently n-HexOH, produced as an unwanted by-product, is typically used to reduce fuel load in ovens or similar processes. However, increasing the value of n-HexOH by conversion to higher alcohols such as 1-OctOH and DeOH would help to improve the economics of the processes in question.

The 1-octanol can be produced naturally, from fats, oils and waxes of animal or plant origin, as well as synthetically, through petrochemicals such as olefins and paraffins.

The development of catalysts has been of great importance in improving 1-octanol synthesis processes, enabling an increase in yields and a reduction in reaction times, and consequently reducing the costs of these industrial processes. Patent applications EP2679304A1 and EP2679303A1 describe a procedure for obtaining a metal oxide type catalyst that comprises gallium and a noble metal for the process of converting lower alcohols to higher alcohols (specifically methanol, ethanol, propanol or isopropanol to n-butanol) which increases the selectivity of the reaction to n-butanol and productivity of n-butanol. It has been discovered that precisely this type of catalyst, when put in contact with ethanol and n-hexanol, results in the production of higher alcohols, mainly 1-octanol.

DESCRIPTION OF THE INVENTION

The present invention relates to a process for obtaining 1-octanol from ethanol and n-hexanol in the presence of a metal oxide catalyst derived from a hydrotalcite, wherein the catalyst comprises Ga and/or V jointly with a noble metal, preferably the noble metal is Pd.

Moreover, the present invention also relates to the process for obtaining a catalyst derived from a hydrotalcite wherein the catalyst comprises V or V/Ga and a noble metal, preferably the noble metal is Pd.

The invention presents the following advantages with respect to the state of the art:
- at a given concentration of noble metal, preferably the noble metal is palladium), the hydrotalcite-derived catalysts that comprise gallium and/or vanadium in their structure provide higher yields of 1-octanol than their analogues without gallium and/or vanadium;
- they are more stable under reaction conditions than their analogues without and/or vanadium;
- a lower temperature is required in order to perform the process.
- they are more selective to the production of linear alcohols reducing the amount of ramified alcohols.

Therefore, a first aspect of the present invention relates to a process for obtaining 1-octanol which comprises a contact step between ethanol, n-hexanol and a catalyst, wherein said catalyst comprises:
 i) a metal oxide that comprises the following metals:
  M1 is at least one bivalent metal selected from Mg, Zn, Cu, Co, Mn, Fe, Ni and Ca;
  M2 is at least one trivalent metal selected from Al, La, Fe, Cr, Mn, Co, Ni, and Ga;
 ii) a noble metal selected from Pd, Pt, Ru, Rh and Re; and
 iii) optionally, comprises V;
with the proviso that the catalyst comprises at least V, Ga or any of its combinations.

"Bivalent metal" or "trivalent metal" is understood to mean a metallic cation with a +2 or +3 charge, respectively.

In a first embodiment of the first aspect of the present invention, the catalyst is obtained by a process comprising the following steps:

a) total or partial thermal decomposition of a hydrotalcite with the formula

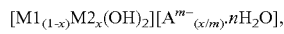

where M1 and M2 have been defined previously; A is at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II), x is a value greater than 0 and less than 1; preferably x is a value between 0.1 and 0.8, m is an integer between 1 and 4; and n is greater than 0, preferably n is a value between 0 and 100, and, more preferably, between 0 and 20;
b) addition to the metal oxide obtained in step a) of at least one noble metal selected from Pd, Pt, Ru, Rh and Re; and optionally, V;
with the proviso that the catalyst comprises V, Ga or any of its combinations.

n indicates the number of crystallisation water molecules and is dependent on the composition of the hydrotalcite cations.

"Hydrotalcite" is understood to mean the structural family of laminar mixed hydroxides with the formula described above. The general structure of hydrotalcites is well-known to persons skilled in the art.

The term "thermal decomposition" is understood to mean a chemical decomposition or structural change caused by the action of heat. This decomposition may be total or partial, depending on whether said decomposition is performed to completion or, on the contrary, is partially performed. This thermal decomposition may be performed at temperatures greater than 150° C. and in the presence of an oxidising or a non-oxidising gas.

In another embodiment of the first aspect of the present invention, the hydrotalcite as described above is obtained by the co-precipitation of M1 and M2 compounds.

Preferably, the co-precipitation is performed in the aqueous phase. The co-precipitation of the compounds may be preferably performed following the addition of a solution of at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II) to a solution of at least one M1 compound and at least one compound of M2. This anion may be introduced between the sheets of the resulting hydrotalcite. In order to obtain solutions of the anion, sodium and/or potassium salts thereof may be used. Preferably, the at least one anion is selected from carbonate, bicarbonate and hydroxide. The best results are obtained when the co-precipitation is performed at a pH higher than 7, preferably between 10 and 14. Moreover, in order to regulate the pH, sodium and/or potassium hydroxide are preferably used.

Preferably, prior to the precipitation of said compounds, there is dissolution of at least one M1 compound and at least one compound of M2. Soluble M1 and M2 compounds is understood to mean any salt that, when in contact with a solvent, is dissociated, preferably a polar solvent, more preferably water. Examples of soluble M1 and M2 compounds may be nitrates, halides, sulfates, carboxylates and, in general, oxoacids that comprise M1 or M2; preferably, the soluble M1 and M2 compounds are nitrates.

In another embodiment of the first aspect of the present invention, M1 comprises Mg, preferably, M1 is Mg.

In another embodiment of the first aspect of the present invention, M2 comprises Al, Ga or any of its combinations. In another embodiment of the first aspect of the present invention, M2 comprises Al. In another embodiment of the first aspect of the present invention, M2 comprises Al and Ga.

In another embodiment of the first aspect of the present invention, M1 comprises Mg, M2 comprises Al and the Mg/Al molar ratio is between 3 and 4.

In another embodiment of the first aspect of the present invention, M1 is Mg, M2 is Al and Ga and the catalyst comprises V.

In another embodiment of the first aspect of the present invention, M1 is Mg, M2 is Al and the catalyst comprises V.

In another embodiment of the first aspect of the present invention, M1 is Mg, M2 comprises Ga and the catalyst does not comprise V.

As regards the anion, A is preferably at least one anion selected from the list that comprises $CO_3^{2-}$, $HCO_3^-$, $O_2^-$, $OH^-$, $Cl^-$, $NO_3^-$, $Cl^-$, $F^-$, $Br^-$, $I^-$, $ClO_4$, $CH_3COO^-$, $C_6H_5COO^-$, and $SO_4^{2-}$; even more preferably, $CO_3^{2-}$, $HCO_3^-$, $O_2^-$ and $OH^-$.

The gels resulting from the co-precipitation as described above are filtered, washed with water and adequately dried. The presence of a hydrotalcite-type structure may be corroborated by means of X-ray diffraction analysis (XRD), whilst the composition (quantity and type of constituent) of the hydrotalcite or the corresponding mixed oxide obtained by thermal decomposition of the aforementioned hydrotalcite may be determined by means of inductive coupled plasma mass spectrometry (ICP-MS) and chemical analysis, amongst others.

In another embodiment of the first aspect of the present invention, thermal decomposition of hydrotalcite is performed by means of calcination under atmosphere of oxygen, nitrogen or any mixture thereof at a temperature ranging between 250° C. and 650° C., preferably between 350° C. and 550° C. The thermal decomposition of hydrotalcite is preferably performed for an interval of 0.5 to 48 hours, preferably between 1 and 24 hours. This process may be performed by heating the hydrotalcite in a gaseous atmosphere and may be performed in a static oven or a calcination reactor with a controlled gas flow, the latter being the preferred system. The gas may be an oxidising gas or a non-oxidising gas. Examples of oxidising gases may include air and oxygen. Examples of non-oxidising gases may be inert gases, such as nitrogen, argon, helium and reducing gases, such as, for example, carbon dioxide, hydrogen and ammonia. Preferably, the calcination is performed in the presence of oxygen, nitrogen or mixtures thereof, and, even more preferably, in the presence of oxygen and nitrogen.

In another embodiment of the first aspect of the present invention, the V and/or the noble metal is added to the metal oxide by wet impregnation, incipient volume impregnation or deposition-precipitation, preferably the V and the noble metal are added to the metal oxide by wet impregnation, incipient volume impregnation or deposition-precipitation, more preferably by incipient volume impregnation. The incipient volume impregnation method, also called incipient wetness impregnation method, is based on the use of a minimum quantity of liquid for the impregnation, only that which is necessary to reach the maximum saturation of the corresponding solid.

In another embodiment of the first aspect of the present invention, the noble metal comprises Pd, preferably the noble metal is Pd. The best yields to 1-octanol have been obtained when the calcined hydrotalcites containing Ga and/or V are impregnated with Pd.

At a given concentration of noble metal, preferably the noble metal is palladium, the hydrotalcite-derived catalysts that comprise gallium and/or vanadium in their structure provide higher yields of 1-octanol in a nitrogen atmosphere than their analogues without gallium/vanadium.

Another embodiment of the first aspect of the present invention is the process as described above, where the concentration of the noble metal in the catalyst ranges between 0.001% and 10% by weight with respect to the total catalyst, preferably between 0.01% and 5%.

In another embodiment of the first aspect of the present invention the concentration of vanadium ranges between 0.001% and 10% by weight with respect to the total catalyst, preferably between 0.01% and 5%.

Another embodiment of the first aspect of the present invention relates to a process for obtaining 1-octanol which comprises a contact step between ethanol, n-hexanol and a catalyst, wherein said catalyst comprises:
  i) a metal oxide that comprises the following metals:
    M1 is at least one bivalent metal selected from Mg, Zn, Cu, Co, Mn, Fe, Ni and Ca;
    M2 is at least one trivalent metal selected from Al, La, Fe, Cr, Mn, Co, Ni, and Ga;
  ii) a noble metal selected from Pd, Pt, Ru, Rh and Re; and
  iii) optionally, comprises V;
with the proviso that the catalyst comprises at least V, Ga or any of its combinations;
wherein the concentration of vanadium ranges between 0.001% and 10% by weight with respect to the total catalyst, preferably between 0.01% and 5%.

In another embodiment of the first aspect of the present invention, following the addition of the noble metal, there is a calcination step. This calcination is preferably calcination in an atmosphere of oxygen, nitrogen or any mixture thereof. This calcination is preferably performed at a temperature ranging between 250° C. and 650° C., and, even more preferably, between 350° C. and 550° C. This calcination is preferably performed for an interval ranging between 0.5 and 48 hours, preferably between 1 and 24 hours, and, even more preferably, between 1 and 6 hours. This process may be performed by heating the hydrotalcite-derived material in a gaseous atmosphere and may be performed in a static oven or a calcination reactor with a controlled gas flow, the latter being the preferred system. The gas may be an oxidising gas or a non-oxidising gas. Examples of oxidising gases may include air and oxygen. Examples of non-oxidising gases may be inert gases, such as nitrogen, argon, helium and reducing gases, such as, for example, carbon dioxide, hydrogen and ammonia. Preferably, the calcination is performed in the presence of oxygen, nitrogen or mixtures thereof, and, even more preferably, in the presence of oxygen and nitrogen.

In a preferred embodiment of the first aspect of the present invention, the process of the invention as described above further comprises a reduction step following the calcination after the addition of the noble metal. During the reduction, the noble metal, which acts as one of the main active sites in the process, is reduced. This reduction step is preferably performed in an $H_2$ atmosphere and, preferably, at a temperature ranging between 200° C. and 500° C., more preferably between 250° C. and 450° C. This reduction is preferably performed for an interval of between 0.5 and 48 hours, preferably between 1 and 24 hours, and, even more preferably, between 1 and 6 hours. Preferably, the reduction takes place immediately prior to the contact step with the reagent.

In another embodiment of the first aspect of the present invention, following the addition of the noble metal, there is a calcination step and a reduction step subsequent to said calcination.

In another preferred embodiment of the first aspect of the invention, contact between the ethanol, the n-hexanol and the catalyst is performed in a reactor selected from the list that comprises discontinuous reactor, continuous stirred-tank reactor, fixed-bed continuous reactor and fluidized-bed continuous reactor, preferably a discontinuous reactor.

In the particular embodiment of the first aspect of the invention, the reactor is a discontinuous reactor, contact between the reagent and the catalyst is performed at a temperature ranging between 50° C. and 450° C., preferably between 130° C. and 330° C. In this process, the weight ratio between the reagent and the catalyst is preferably between 2 and 200, preferably between 5 and 100. Moreover, it is performed for a time interval ranging between 2 minutes and 200 hours, preferably between 1 hour and 100 hours.

In another embodiment of the first aspect of the present invention, the contact between the ethanol, n-hexanol and the catalyst is performed at a pressure of up to 120 bar, preferably between 20 and 80 bar.

In another embodiment of the first aspect of the present invention, the contact between the ethanol, n-hexanol and the catalyst is performed under atmosphere of nitrogen, argon, hydrogen or any mixture thereof, preferably in a nitrogen and hydrogen atmosphere. Usually, higher selectivities to 1-octanol are obtained in the presence of hydrogen.

A second aspect of the present invention relates to a process for obtaining a catalyst, which comprises the following steps:
a) total or partial thermal decomposition of a hydrotalcite with the formula

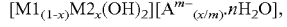

$$[M1_{(1-x)}M2_x(OH)_2][A^{m-}{}_{(x/m)}\cdot nH_2O],$$

to obtain a metal oxide, wherein M1 is at least one bivalent metal selected from Mg, Zn, Cu, Co, Mn, Fe, Ni and Ca; M2 is at least one trivalent metal selected from Al, La, Fe, Cr, Mn, Co, Ni and Ga; and A is at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II),
x is a value greater than 0 and less than 1, preferably x is a value between 0.1 and 0.8; m is an integer between 1 and 4; and n is greater than 0, preferably n is a value between 0 and 100, and, even more preferably, between 0 and 20;
b) addition of V and of at least one noble metal selected from Pd, Pt, Ru, Rh and Re to the solid obtained in the previous step.

n indicates the number of crystallisation water molecules and is dependent on the composition of the hydrotalcite cations.

In one embodiment of the second aspect of the present invention, the process for obtaining a catalyst as described above further comprises a step (a') prior to step (a), where the hydrotalcite is synthesised by the co-precipitation of M1 and M2 compounds.

Preferably, the co-precipitation is performed in the aqueous phase. The co-precipitation of the compounds may be preferably performed following the addition of a solution of at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II) to a solution of at least one M1 compound and at least one compound of M2. This anion may be introduced between the sheets of the resulting hydrotalcite. In order to obtain solutions of the anion, sodium and/or potassium salts thereof may be used. Preferably, the at least one anion is selected from carbonate, bicarbonate and hydroxide. The best results are obtained when the co-precipitation is performed at a pH higher than 7, preferably between 10 and 14. Moreover, in order to regulate the pH, sodium and/or potassium hydroxide are preferably used.

Preferably, prior to the precipitation of said compounds, there is a dissolution of at least one M1 compound and at least one compound of M2. Soluble M1 and M2 compounds is understood to mean any salt that, when in contact with a solvent, is dissociated, preferably a polar solvent, more preferably water. Examples of soluble M1 and M2 compounds may be nitrates, halides, sulfates, carboxylates and, in general, oxoacids that comprise M1 or M2; preferably, the soluble M1 and M2 compounds are nitrates.

In another embodiment of the second aspect of the present invention, M1 comprises Mg, preferably, M1 is Mg.

In another embodiment of the second aspect of the present invention, M2 comprises Al, Ga or any of its combinations. In another embodiment of the second aspect of the present invention, M2 comprises Al. In another embodiment of the second aspect of the present invention, M2 comprises Al and Ga.

In another embodiment of the second aspect of the present invention, M1 comprises Mg, M2 comprises Al and the Mg/Al molar ratio is between 3 and 4.

As regards the anion, A is preferably at least one anion selected from the list that comprises $CO_3^{2-}$, $HCO_3^-$, $O_2^-$, $OH^-$, $Cl^-$, $NO_3^{2-}$, $Cl^-$, $F^-$, $Br^-$, $I^-$, $ClO_4^-$, $CH_3COO^-$, $C_6H_5COO^-$, and $SO_4^{2-}$; even more preferably, $CO_3^{2-}$, $HCO_3^-$, $O_2^-$ and $OH^-$.

In another embodiment of the second aspect of the present invention the thermal decomposition of step (a) is calcination in an atmosphere of oxygen, nitrogen or any mixture thereof at a temperature ranging between 250° C. and 650° C., preferably between 350° C. and 550° C. The thermal decomposition of hydrotalcite is preferably performed for an interval of 0.5 to 48 hours, preferably between 1 and 24 hours. This process may be performed by heating the hydrotalcite in a gaseous atmosphere and may be performed in a static oven or a calcination reactor with a controlled gas flow, the latter being the preferred system. The gas may be an oxidising gas or a non-oxidising gas. Examples of oxidising gases may include air and oxygen. Examples of non-oxidising gases may be inert gases, such as nitrogen, argon, helium and reducing gases, such as, for example, carbon dioxide, hydrogen and ammonia. Preferably, the calcination is performed in the presence of oxygen, nitrogen or mixtures thereof, and, even more preferably, in the presence of oxygen and nitrogen.

In another embodiment of the second aspect of the present invention, the addition of V and/or the addition of the noble metal of step (b) is performed by wet impregnation, incipient volume impregnation or deposition-precipitation, preferably the V and the noble metal are added to the metal oxide by wet impregnation, incipient volume impregnation or deposition-precipitation, more preferably by incipient volume impregnation. In another embodiment of the second aspect of the present invention, the noble metal that is added in step (b) comprises Pd, preferably the noble metal is Pd. The best yields to 1-octanol have been obtained when the calcined hydrotalcites containing V are impregnated with Pd.

At a given concentration of palladium, the hydrotalcite-derived catalysts that comprise vanadium or vanadium and gallium in their structure provide higher yields of 1-octanol in a nitrogen atmosphere than their analogues without vanadium.

Another embodiment of the second aspect of the present invention the concentration of the noble metal in the catalyst ranges between 0.001% and 10% by weight with respect to the total catalyst, preferably between 0.01% and 5%.

Another embodiment of the second aspect of the present invention the concentration of vanadium ranges between 0.001% and 10% by weight with respect to the total catalyst, preferably between 0.01% and 5%.

In another embodiment of the second aspect of the present invention, relates to a process for obtaining a catalyst, which comprises the following steps:

a) total or partial thermal decomposition of a hydrotalcite with the formula

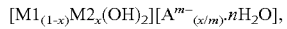

$$[M1_{(1-x)}M2_x(OH)_2][A^{m-}_{(x/m)} \cdot nH_2O],$$

to obtain a metal oxide, wherein M1 is at least one bivalent metal selected from Mg, Zn, Cu, Co, Mn, Fe, Ni and Ca; M2 is at least one trivalent metal selected from Al, La, Fe, Cr, Mn, Co, Ni and Ga; and A is at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II), x is a value greater than 0 and less than 1, preferably x is a value between 0.1 and 0.8; m is an integer between 1 and 4; and n is greater than 0, preferably n is a value between 0 and 100, and, even more preferably, between 0 and 20;

b) addition of V and of at least one noble metal selected from Pd, Pt, Ru, Rh and Re to the solid obtained in the previous step;

wherein the concentration of vanadium ranges between 0.001% and 10% by weight with respect to the total catalyst, preferably between 0.01% and 5%.

In another embodiment of the second aspect of the present invention, the process of obtainment of the catalyst as described above further comprises a step (c), subsequent to (b), where the product obtained in step (b) is calcined, preferably further comprises a reduction step (d), subsequent to (c).

This calcination is preferably calcination in an atmosphere of oxygen, nitrogen or any mixture thereof. This calcination is preferably performed at a temperature ranging between 250° C. and 650° C., and, even more preferably, between 350° C. and 550° C. This calcination is preferably performed for an interval ranging between 0.5 and 48 hours, preferably between 1 and 24 hours, and, even more preferably, between 1 and 6 hours. This process may be performed by heating the hydrotalcite-derived material in a gaseous atmosphere and may be performed in a static oven or a calcination reactor with a controlled gas flow, the latter being the preferred system. The gas may be an oxidising gas or a non-oxidising gas. Examples of oxidising gases may include air and oxygen. Examples of non-oxidising gases may be inert gases, such as nitrogen, argon, helium and reducing gases, such as, for example, carbon dioxide, hydrogen and ammonia. Preferably, the calcination is performed in the presence of oxygen, nitrogen or mixtures thereof, and, even more preferably, in the presence of oxygen and nitrogen.

During the reduction, the noble metal, which acts as one of the main active sites in the process, is reduced. This reduction step is preferably performed in an $H_2$ atmosphere and, preferably, at a temperature ranging between 200° C. and 500° C., more preferably between 250° C. and 450° C. This reduction is preferably performed for an interval of between 0.5 and 48 hours, preferably between 1 and 24 hours, and, even more preferably, between 1 and 6 hours. Preferably, the reduction takes place immediately prior to the contact step with the reagent.

A third aspect of the present invention relates to a catalyst obtained by means of the process for obtainment of a catalyst as described above.

A fourth aspect of the present invention relates to the use of the catalyst as described above to obtain 1-octanol.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples, drawings are provided by way of illustration and are not intended to be limiting of the present invention.

EXAMPLES

Figure 1:
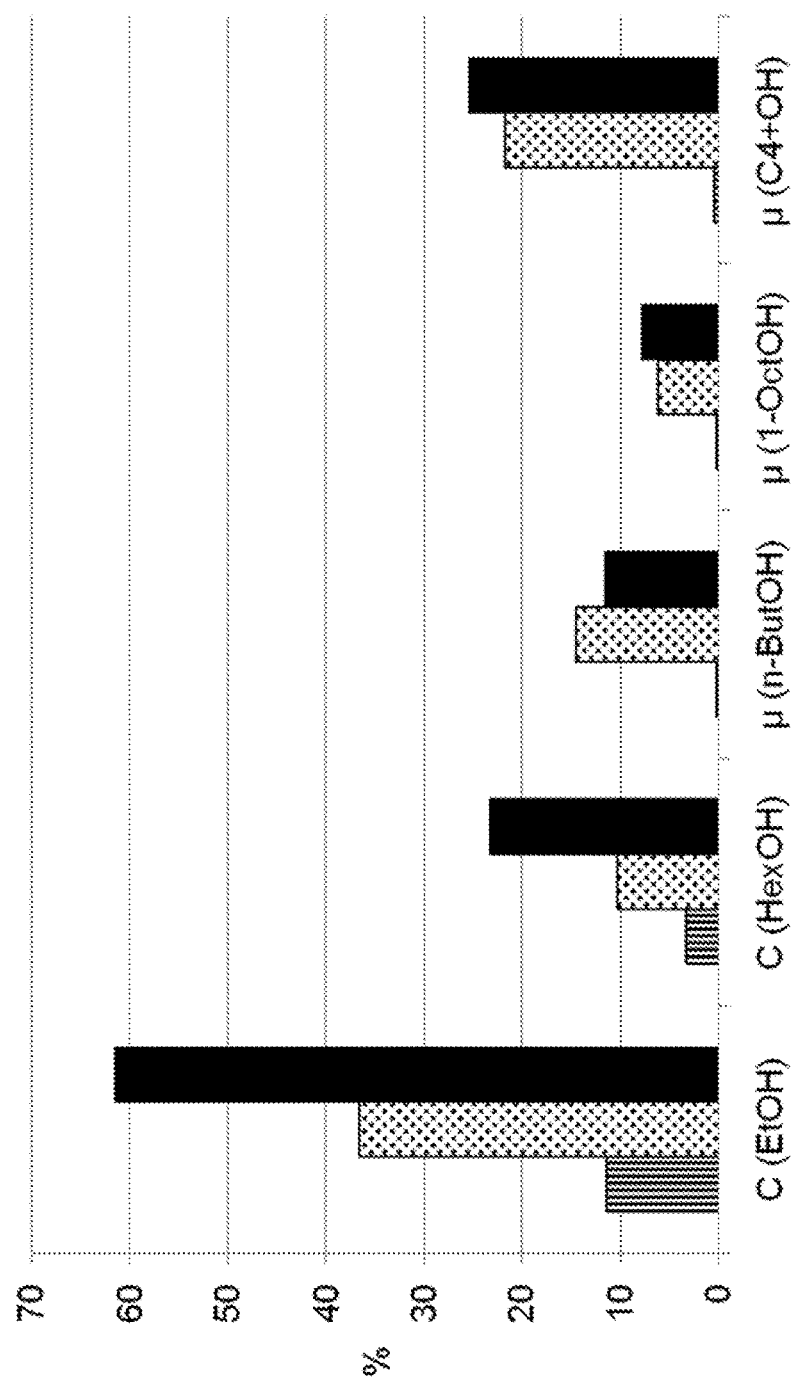
FIG. 1. Shows a comparative graph of the catalytic activities (conversions of EtOH and HexOH and yields to n-ButOH, 1-OctOH and $C_{4+}$OH of catalysts based on a HT-1 material (Examples 1, 4 and 7) in an $N_2$ atmosphere. %: percentage of conversion or yield, as indicated in the x axis; C(EtOH): ethanol conversion, C(HexOH): n-hexanol conversion, μ(n-ButOH): yield to n-ButOH; μ(1-OctOH): yield to 1-octanol; μ(C4+OH): yield to $C_{4+}$ alcohols; Graph key: lines: example 1 (HT-1); dots: example 4 (0.70% Pd/HT-1); black: example 7 (0.77% Pd/0.20% V/HT-1).

Below we will illustrate the invention by means of assays performed by the inventors, which demonstrate the efficacy of the hydrotalcite-derived catalysts that comprise gallium and/or vanadium in their structure in the obtainment of 1-octanol.

Example 1. Synthesis of the HT-1 Catalyst (Mg/Al Molar Ratio≈1)

It was prepared by means of a standard co-precipitation process using two solutions. The first solution contained 17.79 g of $Mg(NO_3)_2.6H_2O$ and 26.05 g of $Al(NO_3)_3.9H_2O$, dissolved in 48.72 g of Milli-Q water, with a molar concentration of Al+Mg of 1.5. The second solution contained 13.95 g of NaOH and 9.86 g of $Na_2CO_3$ in 68.85 g of Milli-Q water, and was used to produce the adequate precipitation of the Al and Mg species, and to set the pH of the total mixture at ≈13. Both solutions were added, at a total flow velocity of 20 ml/h for approx. 4 h, to a container under vigorous stirring at room temperature. The gel formed was aged at room temperature for 1-2 h; thereafter, it was filtered and washed with distilled water until the carbonate was not detected in the filtered liquid (at pH≈7). Subsequently, the solid was dried in an oven at 60° C. for 18 h. The hydrotalcite obtained was calcined in air at 450° C. and a mixed oxide called HT-1 was obtained, with a Mg/Al molar ratio≈1.54 and a surface area (BET method) of 310.37 $m^2/g$. The BET method refers to the Brunauer-Emmett-Teller isotherm method.

Example 2. Synthesis of the HT-3 Catalyst (Mg/Al Molar Ratio≈3)

It was prepared by means of a standard co-precipitation process using two solutions. The first solution contained 27.99 g of $Mg(NO_3)_2.6H_2O$ and 13.65 g of $Al(NO_3)_3.9H_2O$, dissolved in 55.31 g of Milli-Q water, with a molar concentration of Al+Mg of 1.5. The second solution contained 13.13 g of NaOH and 10.23 g of $Na_2CO_3$ in 73.61 g of Milli-Q water, and was used to produce the adequate precipitation of the Al and Mg species, and to set the pH of the total mixture at ≈13. Both solutions were added, at a total flow velocity of 20 ml/h for approx. 4 h, to a container under vigorous stirring at room temperature. The gel formed was aged at room temperature for 1-2 h; thereafter, it was filtered and washed with distilled water until the carbonate was not detected in the filtered liquid (at pH≈7). Subsequently, the solid was dried in an oven at 60° C. for 18 h. The hydrotalcite obtained was calcined in air at 450° C. and a mixed oxide called HT-3 was obtained, with a Mg/Al molar ratio≈3.10 and a surface area (BET method) of 254.03 $m^2/g$.

Example 3. Synthesis of the HT-4 Catalyst (Mg/Al Molar Ratio≈4)

It was prepared by means of a standard co-precipitation process using two solutions. The first solution contained 36.45 g of $Mg(NO_3)_2.6H_2O$ and 13.60 g of $Al(NO_3)_3.9H_2O$, dissolved in 67.79 g of Milli-Q water, with a molar concentration of Al+Mg of 1.5. The second solution contained 12.53 g of NaOH and 16.16 g of $Na_2CO_3$ in 89.63 g of Milli-Q water, and was used to produce the adequate precipitation of the Al and Mg species, and to set the pH of the total mixture at ≈13. Both solutions were added, at a total flow velocity of 20 ml/h for approx. 4 h, to a container under vigorous stirring at room temperature. The gel formed was aged at room temperature for 1-2 h; thereafter, it was filtered and washed with distilled water until the carbonate was not detected in the filtered liquid (at pH≈7). Subsequently, the solid was dried in an oven at 60° C. for 18 h. The hydrotalcite obtained was calcined in air at 450° C. and a mixed oxide called HT-4 was obtained, with a Mg/Al molar ratio≈3.80 and a surface area (BET method) of 257 m$^2$/g.

Example 4. Synthesis of the 0.70% Pd/HT-1 Catalyst

It was prepared from the material prepared as described in Example 1, wherein the incorporation of Pd (1.0% by weight, theoretical) into the HT-1 material (Mg/Al≈1) was performed by means of the incipient wetness impregnation method, using, in this case, 0.0360 g of Pd(NH$_3$)$_4$Cl$_2$.6H$_2$O dissolved in 2 ml of Milli-Q water, to impregnate 1.4086 g of HT-1. Once impregnated, the solid obtained was dried in an oven at 100° C. for 12 h; thereafter, it was calcined in air at 450° C. for 6 h, and, subsequently, it was reduced at 450° C. in an H$_2$ atmosphere for 3 h prior to the catalytic application thereof. The resulting Pd/HT-1 material, characterised by chemical analysis and ICP-MS, contained≈0.70% by weight of Pd.

Example 5. Synthesis of the 0.78% Pd/HT-3 Catalyst

It was prepared from the material prepared as described in Example 2, wherein the incorporation of Pd (1.0% by weight, theoretical) into the HT-3 material (Mg/Al≈3) was performed by means of the incipient wetness impregnation method, using, in this case, 0.0308 g of Pd(NH$_3$)$_4$Cl$_2$.6H$_2$O dissolved in 2 ml of Milli-Q water, to impregnate 1.4030 g of HT-3. Once impregnated, the solid obtained was dried in an oven at 100° C. for 12 h; thereafter, it was calcined in air at 450° C. for 6 h, and, subsequently, it was reduced at 450° C. in an H$_2$ atmosphere for 3 h prior to the catalytic application thereof. The resulting Pd/HT-3 material, characterised by chemical analysis and ICP-MS, contained≈0.78% by weight of Pd.

Example 6. Synthesis of the 0.77% Pd/HT-4 Catalyst

It was prepared from the material prepared as described in Example 3, wherein the incorporation of Pd (1.0% by weight, theoretical) into the HT-4 material (Mg/Al≈1) was performed by means of the incipient wetness impregnation method, using, in this case, 0.030 g of Pd(NH$_3$)$_4$Cl$_2$.6H$_2$O dissolved in 2,000 g of Milli-Q water, to impregnate 1.014 g of HT-4. Once impregnated, the solid obtained was dried in an oven at 100° C. for 14-16 h; thereafter, it was calcined in air at 450° C. for 3-4 h, and, subsequently, it was reduced at 350° C. in an H$_2$ atmosphere for 3 h prior to the catalytic application thereof. The resulting Pd/HT-1 material, characterised by chemical analysis and ICP-MS, contained ≈0.77% by weight of Pd.

Example 7. Synthesis of the 0.77% Pd/0,20% V/HT-1 Catalyst

It was prepared from the material prepared as described in Example 1, wherein the incorporation of Pd (1.0% by weight, theoretical) and of V (0.2% by weight, theorical) into the HT-1 material (Mg/Al≈1) was performed by means of the incipient wetness impregnation method in two successive steps. In the first step, 0.0353 g of Pd(NH$_3$)$_4$Cl$_2$.6H$_2$O dissolved in 2 ml of Milli-Q water were used to impregnate 1.4037 g of HT-1. Once impregnated, the solid obtained was dried in an oven at 100° C. for 12 h. The incorporation of V (0.2%, theorical) to the solid obtained was performed by means of the incipient wetness impregnation method as well, using 0.0098 g of NH$_4$VO$_3$ dissolved in 1 ml of Milli-Q water and 1 ml of oxalic acid 0.2 M to impregnate the solid obtained in the first step. Once impregnated, the solid obtained was dried in an oven at 100° C. for 12 h; thereafter, it was calcined in air at 450° C. for 6 h, and, subsequently, it was reduced at 350° C. in an H$_2$ atmosphere for 3 h prior to the catalytic application thereof. The resulting PdN/HT-1 material, characterised by chemical analysis and ICP-MS, contained ≈0.77% by weight of Pd and 0.2% in weight of V.

Example 8. Synthesis of the 0.75% Pd/0,24% V/HT-3 Catalyst

It was prepared from the material prepared as described in Example 2, wherein the incorporation of Pd (1.0% by weight, theoretical) and of V (0.2% by weight, theorical) into the HT-3 material (Mg/Al≈3) was performed by means of the incipient wetness impregnation method in two successive steps. In the first step, 0.0300 g of Pd(NH$_3$)$_4$Cl$_2$.6H$_2$O dissolved in 2 ml of Milli-Q water were used to impregnate 1.2094 g of HT-3. Once impregnated, the solid obtained was dried in an oven at 100° C. for 12 h. The incorporation of V (0,2%, theorical) to the solid obtained was performed by means of the incipient wetness impregnation method as well, using 0.0084 g of NH$_4$VO$_3$ dissolved in 0.5 ml of Milli-Q water and 1 ml of oxalic acid 0.2 M to impregnate the solid obtained in the first step. Once impregnated, the solid obtained was dried in an oven at 100° C. for 12 h; thereafter, it was calcined in air at 450° C. for 6 h, and, subsequently, it was reduced at 450° C. in an H$_2$ atmosphere for 3 h prior to the catalytic application thereof. The resulting PdN/HT-3 material, characterised by chemical analysis and ICP-MS, contained≈0.75% by weight of Pd and 0.24% in weight of V.

Example 9. Synthesis of the 0.97% Pd/1,00% V/HT-4 Catalyst

It was prepared from the material prepared as described in Example 3, wherein the incorporation of Pd (1.0% by weight, theoretical) and of V (2.00% by weight, theoretical) into the HT-4 material (Mg/Al≈4) was performed by means of the incipient wetness impregnation method in two successive steps. In the first step, 0.0270 g of Pd(NH$_3$)$_4$Cl$_2$.6H$_2$O dissolved in 2.000 g of Milli-Q water were used to impregnate 1.0000 g of HT-4. The incorporation of V (2.0%, theorical) to the solid obtained was performed by means of the incipient wetness impregnation method as well, using 0.0460 g of NH$_4$VO$_3$ dissolved in 2.000 g of Milli-Q water to impregnate the solid obtained in the first step. Once impregnated, the solid obtained was dried in an oven at 100° C. for 14-16 h; thereafter, it was calcined in air at 450° C. for 6 h, and, subsequently, it was reduced at 350° C. in an H$_2$ atmosphere for 3 h prior to the catalytic application thereof. The resulting Pd/V/HT-4 material, characterised by chemical analysis and ICP-MS, contained≈0.97% by weight of Pd and 1.0% in weight of V.

Example 10. Synthesis of the 0.29% Ga-HT-4 Catalyst

It was prepared by means of a standard co-precipitation process using two solutions. The first solution contained 29.89 g of Mg(NO$_3$)$_2$.6H$_2$O, 10.90 g of Al(NO$_3$)$_3$.9H$_2$O and 0.06 g of Ga(NO$_3$)$_3$.9H$_2$O, dissolved in 55.18 g of Milli-Q water, with a molar concentration of (Al+Mg+Ga) of 1.5. The second solution contained 12.52 g of NaOH and 10.52 g of Na$_2$CO$_3$ in 72.60 g of Milli-Q water, and was used to produce the adequate precipitation of the Mg, Al and Ga species, and to set the pH of the total mixture at ≈13. Both solutions were added, at a total flow velocity of 30 ml/h for approximately 4 h, to a container under vigorous stirring at room temperature. The gel formed was aged at room temperature for 1-2 h; thereafter, it was filtered and washed with distilled water until the carbonate was not detected in the filtered liquid (at pH≈7). Subsequently, the solid was dried in an oven at 60° C. for 14-16 h. The hydrotalcite (Ga-HT-4) obtained was calcined in air at 450° C. for 3-4 h, to obtain a mixed oxide with a Mg/Al molar ratio≈3.8, a Ga content of 0.29% by weight (measured by chemical analysis and ICP-MS), and a surface area (BET method) of 262 m$^2$/g.

Example 11. Synthesis of the 0.87% Pd/0.29% Ga-HT-4 Catalyst

It was prepared from the material prepared as described in Example 10, wherein the incorporation of Pd (1.0% by weight, theoretical) into the Ga-HT-4 material was performed by means of the incipient wetness impregnation method, using, in this case, 0.030 g of Pd(NH$_3$)$_4$Cl$_2$.6H$_2$O dissolved in 1.700 g of Milli-Q water, to impregnate 1.100 g of 0.29% Ga-HT-4. Once impregnated, the solid obtained was dried in an oven at 100° C. for 14-16 h; thereafter, it was calcined in air at 450° C. for 3-4 h, and, subsequently, it was reduced at 350° C. in an H$_2$ atmosphere for 3 h prior to the catalytic application thereof. The resulting Pd/0.29% Ga-HT-4 material, characterised by chemical analysis and ICP-MS, contained≈0.87% by weight of Pd.

Example 12. Synthesis of the 0.97% Pd/0.29% V/0.29% Ga-HT-4 Catalyst

It was prepared from the material prepared as described in Example 10, wherein the incorporation of Pd (1.0% by weight, theoretical) and V (0.2% by weight, theorical) into the Ga-HT-4 material was performed by means of the incipient wetness impregnation method in two successive steps. In the first step, 0.0355 g of Pd(NH$_3$)$_4$Cl$_2$.6H$_2$O dissolved in 2 ml of Milli-Q water were used to impregnate 1.4072 g of 0.29% Ga-HT-4. Once impregnated, the solid obtained was dried in an oven at 100° C. for 14-16 h. The incorporation of V (0.2%, theorical) to the solid obtained was performed by means of the incipient wetness impregnation method as well, using 0.0096 g of NH$_4$VO$_3$ dissolved in 1 ml of Milli-Q water and 1 ml of oxalic acid 0.2 M to impregnate the solid obtained in the first step. Once impregnated, the solid obtained was dried in an oven at 100° C. for 1-2 h; thereafter, it was calcined in air at 450° C. for 6 h, and, subsequently, it was reduced at 350° C. in an H$_2$ atmosphere for 3 h prior to the catalytic application thereof. The resulting PdN/0.29% Ga-HT-4 material, characterised by chemical analysis and ICP-MS, contained≈0.97% by weight of Pd and 0.29% of V.

Example 13. Synthesis of the 4.9% Cu-HT-4 Catalyst

This catalyst was synthesised to illustrate hydrotalcite-type catalysts containing Cu, such as those cited in application WO2009026523. Various catalysts were synthesised with different concentrations of Cu, and the catalyst that provided the best results, in terms of selectivity and conversion, was selected in order to be compared to the catalysts of the invention.

It was prepared by means of a standard co-precipitation process using two solutions. The first solution contained 30.0795 g of Mg(NO$_3$)$_2$.6H$_2$O, 10.4441 g of Al(NO$_3$)$_3$.9H$_2$O and 1.1720 g of Cu(NO$_3$)$_2$.3H$_2$O, dissolved in 57.6217 g of Milli-Q water, with a molar concentration of (Al+Mg+Cu) of 1.5. The second solution contained 13.0492 g of NaOH and 10.5207 g of Na$_2$CO$_3$ in 74.7069 g of Milli-Q water, and was used to produce the adequate precipitation of the Mg, Al and Cu species, and to set the pH of the total mixture at 13. Both solutions were added (total flow velocity=30 ml/h for approximately 4 h) to a container under vigorous stirring at room temperature. The gel formed was aged at room temperature for 1-2 h; thereafter, it was filtered and washed with distilled water until the carbonate was not detected in the filtered liquid (at pH≈7). Subsequently, the solid was dried in an oven at 60° C. for 18 h. The hydrotalcite (Cu-HT-4) obtained was calcined in air at 450° C. for 3-4 h, to obtain a mixed oxide with a Mg/Al molar ratio≈3.8, a Cu content of 4.9% by weight, characterised by chemical analysis and ICP-MS and a surface area (BET method) of 190.08 m$^2$/g.

Example 14. Synthesis of the 0.98% Pd/0.20% V/4.9% Cu-HT-4 Catalyst

It was prepared from the material prepared as described in Example 12, wherein the incorporation of Pd (1.0% by weight, theoretical) and V (0.2% by weight, theorical) into the 4.9% Cu-HT-4 material (Mg+Cu/Al≈4) was performed by means of the incipient wetness impregnation method in two successive steps. In the first step, 0.0350 g of Pd(NH$_3$)$_4$Cl$_2$.6H$_2$O dissolved in 2 ml of Milli-Q water were used to impregnate 1.4000 g of 4.9% Cu-HT-4. Once impregnated, the solid obtained was dried in an oven at 100° C. for 12 h. The incorporation of V (0.2%, theorical) to the solid obtained was performed by means of the incipient wetness impregnation method as well, using 0.0090 g of NH$_4$VO$_3$ dissolved in 1 ml of Milli-Q water and 1 ml of oxalic acid 0.2 M to impregnate the solid obtained in the first step. Once impregnated, the solid obtained was dried in an oven at 100° C. for 12 h; thereafter, it was calcined in air at 450° C. for 6 h, and, subsequently, it was reduced at 350° C. in an H$_2$ atmosphere for 3 h prior to the catalytic application thereof. The resulting PdN/0.29% Ga-HT-4 material, characterised by chemical analysis and ICP-MS, contained≈0.98% by weight of Pd and 0.20% of V.

Example 15. Comparative Catalytic Activity of the Catalysts of Examples 1 to 13 Under N$_2$ Atmosphere 1750 mg of ethanol, 1790 mg n-hexanol and 350 mg of one of the catalytic materials of Examples 1-13 were introduced into a 12-ml stainless steel autoclave reactor, with a strengthened PEEK-coated (Polyether ethyl ketone) inside and a magnetic stirrer. The reactor was hermetically closed, and the system contained a connector to a pressure meter (manometer), another connector for the loading of gases and a third outlet which made it possible to take samples at different time intervals. The reactor was initially pressurised with 24 bars of N$_2$, and heated to 250° C. under continuous stirring, until the total system pressure reached approx. 35-40 bars (reaction time=0). Liquid samples (≈50-100 μl)

were taken at different time intervals until 17 hours of reaction. The samples were filtered and diluted in a 2% by weight of chlorobenzene in acetonitrile standard solution, and analysed by means of gas chromatography in a GC-3900 Varian equipped with an FID detector and a 60-m TRB-624 capillary column.

The ethanol conversion, in molar percentage (conv. EtOH), was calculated from the composition of the mixture obtained:

(initial moles of ethanol−final moles of ethanol)/
 (initial moles of ethanol*100)

The n-hexanol conversion, in molar percentage (conv. n-HexOH), was calculated from the composition of the mixture obtained:

(initial moles of $n$-hexanol−final moles of $n$-hexanol)/(initial moles of $n$-hexanol*100)

The total yield of n-butanol, in molar percentage (Yield n-ButOH) was calculated as:

(moles of $n$-butanol/moles of total products)*Conv.EtOH/100

The total yield of 1-octanol, in molar percentage (Yield 1-OctOH) was calculated as:

(moles of 1-octanol/moles of total products)*Conv.EtOH/100

The total yield of linear $C_{4+}$ alcohols, in molar percentage (Yield linear $C_{4+}$OH), which includes n-butanol and 1-octanol of course, was calculated as:

(moles of linear $C_{4+}$/moles of total products)*Conv.EtOH/100

The total yield of branched $C_{4+}$ alcohols, in molar percentage (Yield branched $C_{4+}$OH), was calculated as:

(moles of branched $C_{4+}$/moles of total products)*Conv.EtOH/100

Figure 2:
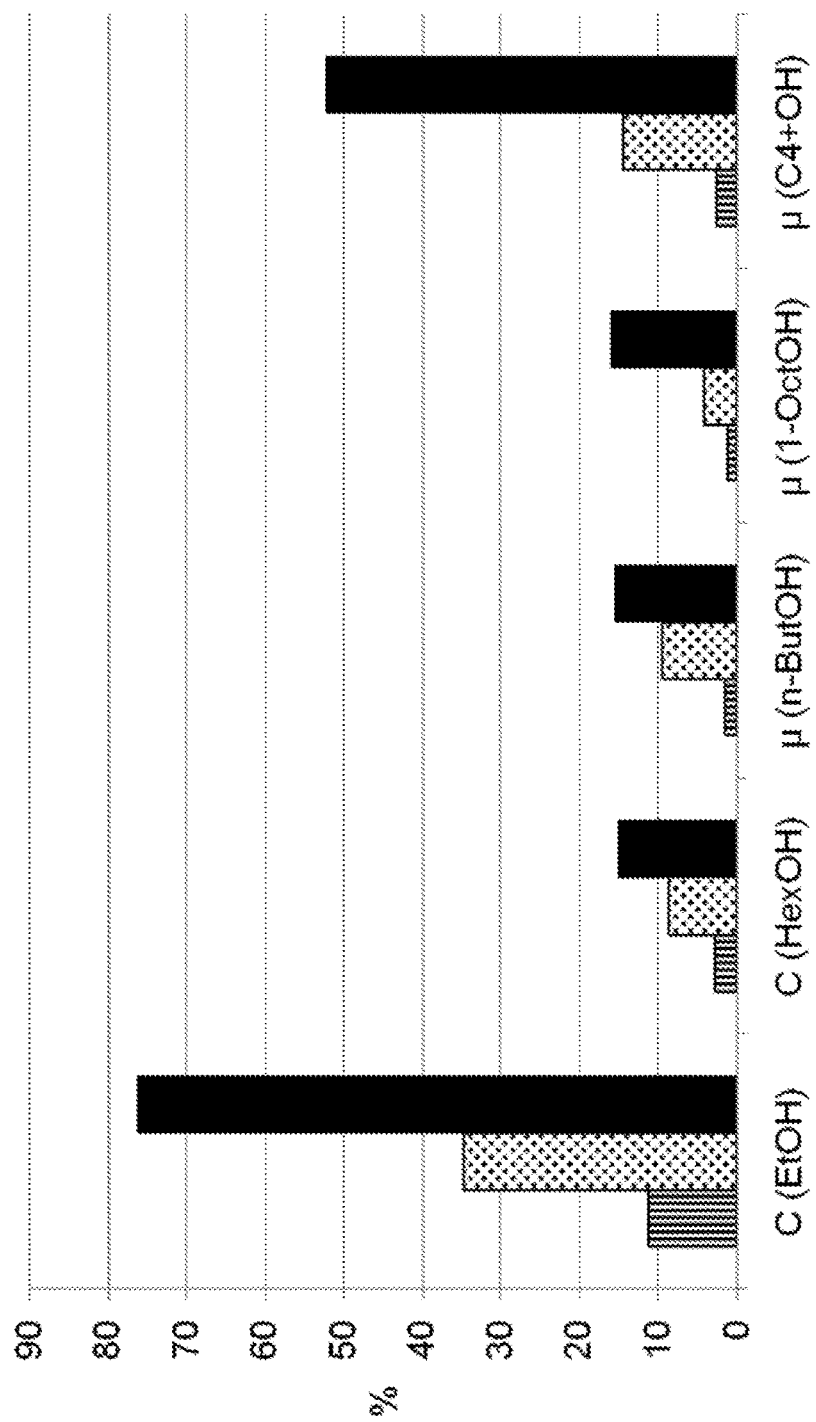
FIG. 2. Shows a comparative graph of the catalytic activities (conversions of EtOH and n-HexOH and yields to n-ButOH, 1-OctOH and $C_{4+}$OH of catalysts based on a HT-3 material (Examples 2, 5 and 8) in an $N_2$ atmosphere. Graph key: lines: example 2 (HT-3); dots: example 5 (0.78% Pd/HT-3); black: example 8 (0.75% Pd/0.24% V/HT-3).
Figure 3:
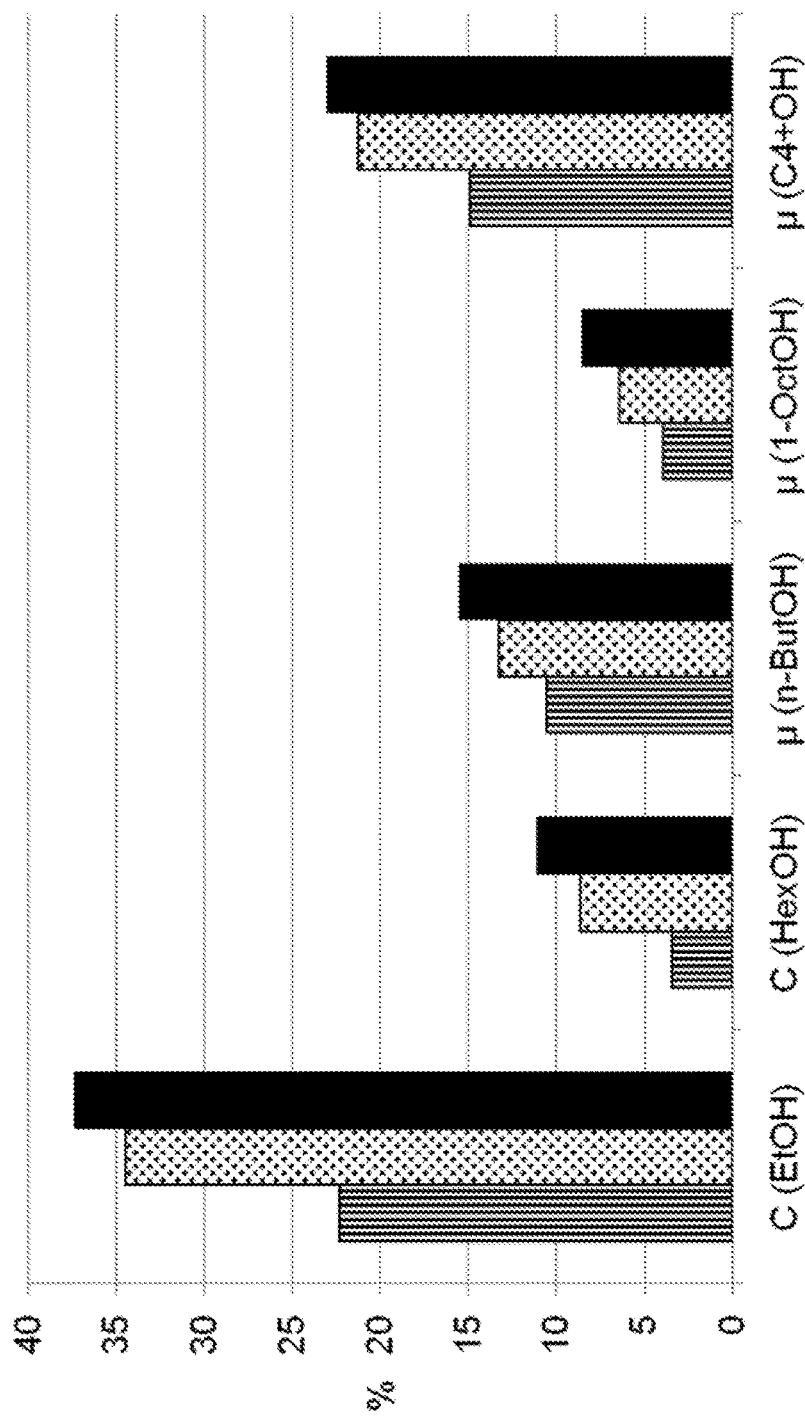
FIG. 3. Shows a comparative graph of the catalytic activities (conversions of EtOH and n-HexOH and yields to n-ButOH, 1-OctOH and $C_{4+}$OH of catalysts based on a HT-4 material (Examples 3, 6 and 9) in an $N_2$ atmosphere. Graph key: lines: example 3 (HT-4); dots: example 6 (0.77% Pd/HT-4); black: example 98 (0.97% Pd/1.0% V/HT-4).

In this manner, the following results were obtained:

These results show that the incorporation of vanadium into hydrotalcite-derived catalysts with different Mg/Al ratio in their structure achieve higher yields both to n-butanol and to 1-octanol, and in general, higher yield to $C_{4+}$ alcohols than their analogue catalyst without vanadium. Not only that but also the catalyst show an improved catalytic activity (ethanol and n-hexanol conversion), even with V concentrations under 1% as it can be seen in FIGS. 1, 2 and 3.

Figure 4:
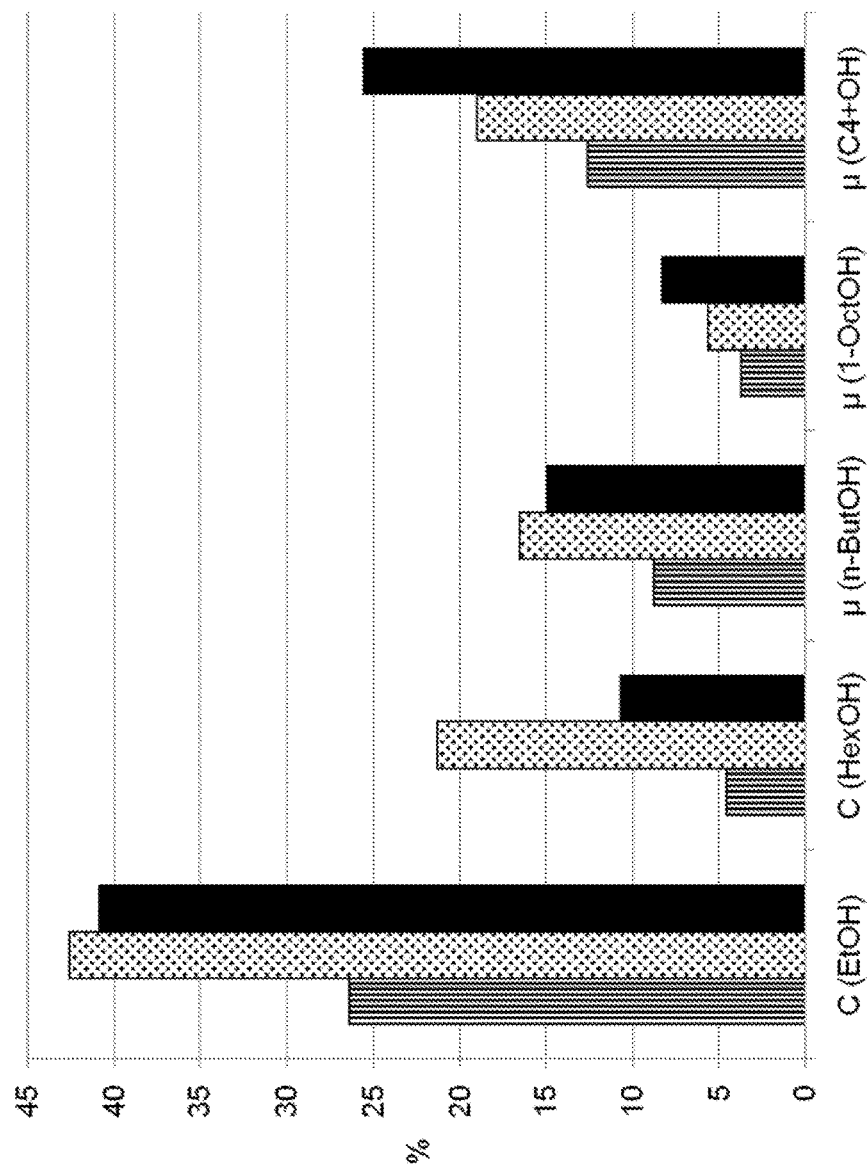
FIG. 4. Shows a comparative graph of the catalytic activities (conversions of EtOH and n-HexOH and yields to n-ButOH, 1-OctOH and $C_{4+}$OH of catalysts based on a HT-4 material with Ga (Examples 10, 11 and 12) in an $N_2$ atmosphere. Graph key: lines: example 10 (0.29% Ga-HT-4); dots: example 11 (0.87% Pd/0.29% Ga-HT-4); black: example 12 (0.97% Pd/0.29% V/0.29% Ga-/HT-4).

Comparison of the results of the examples 3, 6, 9 and 10-12 shows that the incorporation of vanadium into hydrotalcite-derived catalysts comprising Ga in their structure gives higher yields to 1-octanol, and in general, higher yield to $C_{4+}$ alcohols than their analogue catalyst without vanadium. This effect occurs even with V concentrations lower than 0.3%, as it can be seen in FIG. 4. This indicates the higher stability of the catalyst of the invention under reaction conditions.

If we compare the examples 6, 8, 9, 11, 13 and 14, the results show that the incorporation of vanadium into hydrotalcite-derived catalysts with different Mg/Al ratios gives higher yields to 1-octanol, and in general, higher yield to $C_{4+}$ alcohols than their analogue catalyst without vanadium. However, the production of $C_{4+}$OH decreases substantially when the catalyst comprises Cu in their structure, even in the presence of Pd and V. This indicates the higher stability of the catalyst of the invention under reaction conditions.

Example 16. Comparative Catalytic Activity of the Catalysts of Examples 6, 9 and 11 Under $N_2$ Atmosphere with Ethanol Only (without n-Hexanol)

3500 mg of ethanol, and 200 mg of one of the catalytic materials of Examples 6, 9 and 11 were introduced into a 12-ml stainless steel autoclave reactor, with a strengthened PEEK-coated (Polyether ethyl ketone) inside and a magnetic stirrer. The reactor was hermetically closed, and the system contained a connector to a pressure meter (manometer),

TABLE 1

Catalytic activity of different mixed metal oxides in the transformation of ethanol + n-hexanol under nitrogen atmosphere.

| Ex. | Catalyst | T (h) | Conv EtOH | Conv. n-HexOH | Yield n-ButOH | Yield 1-OctOH | Yield $C_{4+}$OH Linear | Yield $C_{4+}$OH branched |
|---|---|---|---|---|---|---|---|---|
| 1 | HT-1 | 5 | 11.4 | 3.3 | 0.25 | 0.18 | 0.4 | 0.0 |
| 2 | HT-3 | 5 | 11.2 | 2.8 | 1.50 | 1.08 | 2.5 | 0.0 |
| 3 | HT-4 | 5 | 22.3 | 3.4 | 10.56 | 3.95 | 14.9 | 0.4 |
| 4 | 0.70% Pd/HT-1 | 5 | 36.6 | 10.3 | 14.50 | 6.20 | 21.7 | 0.9 |
| 5 | 0.78% Pd/HT-3 | 5 | 34.7 | 8.7 | 9.44 | 4.24 | 14.4 | 1.3 |
| 6 | 0.77% Pd/HT-4 | 5 | 34.5 | 8.6 | 13.21 | 6.42 | 21.3 | 1.0 |
| 7 | 0.77% Pd/0.20% V/HT-1 | 5 | 61.6 | 23.2 | 11.61 | 7.82 | 25.4 | 1.4 |
| 8 | 0.75% Pd/0.24% V/HT-3 | 5 | 76.2 | 18.0 | 17.57 | 19.55 | 42.2 | 2.4 |
| 9 | 0.97% Pd/1.0% V/HT-4 | 5 | 37.4 | 11.1 | 15.46 | 8.55 | 23.0 | 1.0 |
| 10 | 0.29% Ga-HT-4 | 5 | 26.4 | 4.6 | 8.77 | 3.78 | 12.6 | 0.4 |
| 11 | 0.87% Pd/0.29% Ga-HT-4 | 5 | 42.6 | 21.3 | 16.52 | 5.69 | 19.0 | 1.1 |
| 12 | 0.97% Pd/0.29% V/0.29% Ga-HT-4 | 5 | 40.9 | 10.7 | 14.93 | 8.30 | 25.6 | 1.1 |
| 13 | 4.9% Cu-HT-4 | 5 | 22.4 | 8.0 | 4.03 | 4.99 | 9.6 | 0.8 |
| 14 | 0.98% Pd/0.20% V/4.9% Cu-HT-4 | 5 | 36.1 | 7.9 | 7.28 | 3.87 | 13.1 | 0.4 | another connector for the loading of gases and a third outlet which made it possible to take samples at different time intervals. The reactor was initially pressurised with 24 bars of $N_2$, and heated to 200° C. under continuous stirring, until the total system pressure reached approx. 30 bars (reaction time=0). Liquid samples (≈50-100 µl) were taken at different time intervals until 17 hours of reaction. The samples were filtered and diluted in a 2% by weight of chlorobenzene in acetonitrile standard solution, and analysed by means of gas chromatography in a GC-3900 Varian equipped with an FID detector and a 60-m TRB-624 capillary column.

The following results were obtained:

TABLE 2

Catalytic activity of different mixed metal oxides in the transformation of ethanol under nitrogen atmosphere.

| Ex. | Catalyst | T (h) | Conv EtOH | Yieldt n-ButOH | Yield n-HexOH | Yield 1-OctOH | Yield $C_{4+}OH$ lineal | Yield $C_{4+}OH$ branched |
|---|---|---|---|---|---|---|---|---|
| 6 | 0.77% Pd/HT-4 | 5 | 15.5 | 11.9 | 1.9 | 0.4 | 14.6 | 0.2 |
| 9 | 0.97% Pd/1.0%V/HT-4 | 5 | 14.0 | 9.4 | 1.8 | 0.2 | 11.6 | 0.1 |

TABLE 2-continued

Catalytic activity of different mixed metal oxides in the transformation of ethanol under nitrogen atmosphere.

| Ex. | Catalyst | T (h) | Conv EtOH | Yieldt n-ButOH | Yield n-HexOH | Yield 1-OctOH | Yield $C_{4+}OH$ lineal | Yield $C_{4+}OH$ branched |
|---|---|---|---|---|---|---|---|---|
| 11 | 0.87% Pd/0.29% Ga-HT-4 | 5 | 15.8 | 12.1 | 1.9 | 0.3 | 14.4 | 0.3 |

The rest of the products up to 100% comprise mainly aldehydes (ethanal, butanal, hexanal, ethylacetate and diethoxyethane.

These results show that the catalyst of the invention with ethanol as a reagent do not yield 1-octanol in a high percentage. It is therefore shown that n-hexanol and ethanol is required to obtain high yields of 1-octanol.

Moreover, the percentage of branched products obtained is higher if no n-hexanol is used.

Example 17. Comparative Catalytic Activity of the Catalysts of Examples 6, 9, 11 and 12 Under $N_2$ Atmosphere with n-Butanol as Feedstock (Neither Ethanol Nor n-Hexanol)

3500 mg of n-butanol, and 350 mg of one of the catalytic materials of Examples 6, 9, 11 and 12 were introduced into a 12-ml stainless steel autoclave reactor, with a strengthened PEEK-coated (Polyether ethyl ketone) inside and a magnetic stirrer. The reactor was hermetically closed, and the system contained a connector to a pressure meter (manometer), another connector for the loading of gases and a third outlet which made it possible to take samples at different time intervals. The reactor was initially pressurised with 24 bars of $N_2$, and heated to 250° C. under continuous stirring, until the total system pressure reached approx. 40 bars (reaction time=0). Liquid samples (≈50-100 µl) were taken at different time intervals until 17 hours of reaction. The samples were filtered and diluted in a 2% by weight of chlorobenzene in acetonitrile standard solution, and analysed by means of gas chromatography in a GC-3900 Varian equipped with an FID detector and a 60-m TRB-624 capillary column.

The following results were obtained:

TABLE 3

Catalytic activity of different mixed metal oxides in the transformation of n-butanol under nitrogen atmosphere.

| Ex. | Catalyst | T (h) | Conv. n-ButOH | Yield Butanal | Yield Aldehydes | Yield 1-OctOH | Yield $C_{4+}OH$ lineal | Yield $C_{4+}OH$ branched |
|---|---|---|---|---|---|---|---|---|
| 6 | 0.77% Pd/HT-4 | 5 | 17.1 | 2.9 | 0.6 | 0.1 | 6.4 | 5.3 |
| 9 | 0.97% Pd/1.0% V/HT-4 | 5 | 35.5 | 1.4 | 0.6 | 0.6 | 22.5 | 6.4 |
| 11 | 0.87% Pd/0.29% Ga-HT-4 | 5 | 32.9 | 1.7 | 0.6 | 0.2 | 21.1 | 6.8 |
| 12 | 0.97% Pd/0.29% V/0.29% Ga-HT-4 | 5 | 25.9 | 1.9 | 0.5 | 0.2 | 14.8 | 6.5 |

The rest of the products up to 100% comprise mainly 3-methyl-2-butanone, butyl butanoate, n-butyl ether, 4-methyl-2-hexanone, 1,1-dibutoxybutane.

These results show that the catalyst of the invention with n-butanol as a reagent do not yield 1-octanol in a high percentage. It is therefore shown that n-hexanol and ethanol is required to obtain high yields of 1-octanol.

Moreover, the percentage of branched products obtained is higher if neither n-hexanol nor ethanol is used.

The invention claimed is:

1. Process for obtaining 1-octanol which comprises a contact step between ethanol, n-hexanol, and a catalyst, wherein the catalyst comprises:
   i) a metal oxide that comprises the following metals:
      M1 is at least one bivalent metal selected from Mg, Zn, Cu, Co, Mn, Fe, Ni, and Ca; and
      M2 is at least one trivalent metal selected from Al, La, Fe, Cr, Mn, Co, Ni, and Ga;
   ii) a noble metal selected from Pd, Pt, Ru, Rh, and Re; and
   iii) optionally, comprises V;
   with the proviso that the catalyst comprises at least V, Ga, or any of its combinations.

2. The process according to claim 1, wherein the catalyst is obtained by a process comprising the following steps:
   a) total or partial thermal decomposition of a hydrotalcite with the formula $[M1_{(1-x)}M2_x(OH)_2][A^{m-}_{(x/m)} \cdot nH_2O]$, where:
   M1 and M2 is defined in claim 1,
   A is at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III), and hexacyanoferrate (II),
   x is a value greater than 0 and less than 1; m is an integer between 1 and 4; and n is greater than 0;
   b) addition to the metal oxide obtained in step a) of:
   at least one noble metal selected from Pd, Pt, Ru, Rh, and Re; and optionally, V;
   with the proviso that the catalyst comprises V, Ga, or any of its combinations.

3. The process according claim 2, wherein the hydrotalcite is obtained by the co-precipitation of M1 and M2 compounds.

4. The process according to claim 1, wherein M1 is Mg.

5. The process according to claim 1, wherein M2 comprises Al, Ga or any of its combinations.

6. The process according to claim 1, wherein the catalyst comprises V.

7. The process according to claim 2, wherein the thermal decomposition of hydrotalcite is performed by means of calcination under atmosphere of oxygen, nitrogen, or any mixture thereof at a temperature ranging between 250° C. and 650° C.

8. The process according to claim 2, wherein A is at least one anion selected from $CO_3^{2-}$, $HCO_3^-$, $O_2^-$, and $OH^-$.

9. The process according to claim 2, wherein the V and/or the noble metal is added to the metal oxide by wet impregnation, incipient volume impregnation, or deposition-precipitation.

10. The process according to claim 2, wherein, following the addition of the noble metal, there is a calcination step and a reduction step subsequent to said calcination.

11. The process according to claim 1, wherein the contact between the ethanol, n-hexanol, and the catalyst is performed at a pressure of up to 120 bar.

12. The process according to claim 1, wherein the contact between the ethanol, n-hexanol, and the catalyst is performed under atmosphere of nitrogen, argon, hydrogen, or any mixture thereof.

13. Process for obtaining a catalyst described according to claim 1, which comprises the following steps:
   a) total or partial thermal decomposition of a hydrotalcite with the formula $[M1_{(1-x)}M2_x(OH)_2][A^{m-}_{(x/m)} \cdot nH_2O]$, to obtain a metal oxide, wherein:
   M1 is at least one bivalent metal selected from Mg, Zn, Cu, Co, Mn, Fe, Ni, and Ca;
   M2 is at least one trivalent metal selected from Al, La, Fe, Cr, Mn, Co, Ni, and Ga; and
   A is at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III), and hexacyanoferrate (II),
   x is a value greater than 0 and less than 1; m is an integer between 1 and 4; and n is greater than 0,
   b) addition of V and of at least one noble metal selected from Pd, Pt, Ru, Rh, and Re to the solid obtained in the previous step (a).

14. The process according to claim 13, characterised in that it further comprises a step (a') prior to step (a), where the hydrotalcite is synthesised by the co-precipitation of M1 and M2 compounds.

15. The process according to claim 13, wherein the thermal decomposition of step (a) is calcination in an atmosphere of oxygen, nitrogen or any mixture thereof at a temperature ranging between 250° C. and 650° C.

16. The process according to claim 13, wherein the addition of
   V and/or the addition of the noble metal of step (b) is performed by wet impregnation, incipient volume impregnation, or deposition-precipitation.

17. The process according to claim 13, wherein M1 is Mg.

18. The process according to claim 13, wherein M2 comprises Al, Ga, or any of its combinations.

19. The process according to claim 13, where A is at least one anion selected from $CO_3^{2-}$, $HCO_3^-$, $O_2^-$, and $OH^-$.

20. The process according to claim 13, wherein the noble metal that is added in step (b) is Pd.

21. The process according to claim 13, which further comprises a step (c), subsequent to (b), where the product obtained in step (b) is calcined.

22. The process according to claim 21, which further comprises a reduction step (d), subsequent to (c).

23. A catalyst obtained by means of the process according to claim 13.

24. A method for obtaining 1-octanol which comprises a contact step between ethanol, n-hexanol, and a catalyst as described in claim 23.

* * * * *